United States Patent
Pastore et al.

(10) Patent No.: US 8,311,630 B2
(45) Date of Patent: Nov. 13, 2012

(54) REDUCTION OF AV DELAY FOR TREATMENT OF CARDIAC DISEASE

(75) Inventors: Joseph M. Pastore, Concord, OH (US); Rodney W. Salo, Fridley, MN (US); Julio C. Spinelli, Lakewood Ranch, FL (US); Allan C. Shuros, St. Paul, MN (US); Andres Belalcazar, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/229,948

(22) Filed: Sep. 12, 2011

(65) Prior Publication Data

US 2011/0319955 A1    Dec. 29, 2011

Related U.S. Application Data

(63) Continuation of application No. 11/615,383, filed on Dec. 22, 2006, now Pat. No. 8,019,416, which is a continuation-in-part of application No. 11/561,049, filed on Nov. 17, 2006, now Pat. No. 7,941,216, and a continuation-in-part of application No. 11/559,131, filed on Nov. 13, 2006.

(51) Int. Cl.
*A61N 1/365* (2006.01)
(52) U.S. Cl. .......................................... 607/9
(58) Field of Classification Search .................. 607/9
See application file for complete search history.

(56) References Cited

U.S. PATENT DOCUMENTS

| | | | |
|---|---|---|---|
| 3,943,936 A | 3/1976 | Rasor et al. |
| 4,884,575 A | 12/1989 | Sanders |
| 4,945,909 A | 8/1990 | Fearnot et al. |
| 5,024,222 A | 6/1991 | Thacker |
| 5,186,169 A | 2/1993 | Schaldach |
| 5,372,607 A | 12/1994 | Stone et al. |
| 5,411,535 A | 5/1995 | Fujii et al. |
| 5,466,245 A | 11/1995 | Spinelli et al. |
| 5,487,752 A | 1/1996 | Salo et al. |
| 5,919,209 A | 7/1999 | Schouten |
| 6,144,866 A | 11/2000 | Miesel et al. |

(Continued)

FOREIGN PATENT DOCUMENTS

WO    WO-9743001 A1    11/1997

(Continued)

OTHER PUBLICATIONS

U.S. Appl. No. 11/615,383, filed Dec. 22, 2006, Pastore, Joseph, et al.

(Continued)

*Primary Examiner* — Carl H Layno
*Assistant Examiner* — Jeremiah Kimball
(74) *Attorney, Agent, or Firm* — Schwegman Lundberg & Woessner, P.A.

(57) ABSTRACT

An implantable pacing device for delivering ventricular pacing may be configured to intermittently reduce the AVD interval for beneficial effect in patients with compromised ventricular function (e.g., HF patients and post-MI patients). The AVD interval may be reduced in an AVD reduction mode, by shortening the AVD in an atrial triggered ventricular pacing mode or by switching to a non-atrial triggered ventricular pacing mode (e.g., VVI) and delivering paces at a rate above the intrinsic rate. The physiological effects of AVD reduction may be either positive or negative on cardiac output, depending upon the individual patient.

20 Claims, 6 Drawing Sheets

U.S. PATENT DOCUMENTS

| | | | |
|---|---|---|---|
| 6,208,900 B1 | 3/2001 | Ecker et al. |
| 6,253,107 B1 | 6/2001 | Albrecht et al. |
| 6,498,950 B1 | 12/2002 | Bradley |
| 6,507,756 B1 | 1/2003 | Heynen et al. |
| 6,553,259 B2 | 4/2003 | Mouchawar et al. |
| 6,580,946 B2 | 6/2003 | Struble |
| 6,628,988 B2 | 9/2003 | Kramer et al. |
| 6,754,530 B2 | 6/2004 | Bakels et al. |
| 6,804,552 B2 | 10/2004 | Thompson et al. |
| 6,859,667 B2 | 2/2005 | Goode |
| 6,865,420 B1 | 3/2005 | Kroll |
| 6,875,180 B2 | 4/2005 | Weiner et al. |
| 6,885,890 B2 | 4/2005 | Spinelli et al. |
| 6,912,422 B1 | 6/2005 | Obel et al. |
| 6,915,160 B2 | 7/2005 | Auricchio et al. |
| 6,937,901 B2 | 8/2005 | Zhu et al. |
| 6,950,701 B2 | 9/2005 | Begemann et al. |
| 6,965,797 B2 | 11/2005 | Pastore et al. |
| 6,973,349 B2 | 12/2005 | Salo |
| 7,016,726 B1 | 3/2006 | Picardo et al. |
| 7,065,405 B2 | 6/2006 | Pastore et al. |
| 7,139,613 B2 | 11/2006 | Reinke et al. |
| 7,174,219 B2 | 2/2007 | Wahlstrand et al. |
| 7,177,698 B2 | 2/2007 | Klosterman et al. |
| 7,184,835 B2 | 2/2007 | Kramer et al. |
| 7,190,245 B2 | 3/2007 | Receveur et al. |
| 7,194,307 B2 | 3/2007 | Salo et al. |
| 7,203,540 B2 | 4/2007 | Ding et al. |
| 7,215,997 B2 | 5/2007 | Yu et al. |
| 7,225,025 B2 | 5/2007 | Goode |
| 7,236,834 B2 | 6/2007 | Christopherson et al. |
| 7,363,077 B1 | 4/2008 | Min et al. |
| 7,383,086 B2 | 6/2008 | Ding |
| 7,392,084 B2 | 6/2008 | KenKnight et al. |
| 7,450,988 B2 | 11/2008 | Ross et al. |
| 2002/0087694 A1 | 7/2002 | Daoud et al. |
| 2003/0083700 A1 | 5/2003 | Hill |
| 2003/0149456 A1 | 8/2003 | Rottenberg et al. |
| 2004/0093034 A1 | 5/2004 | Girouard et al. |
| 2004/0133247 A1 | 7/2004 | Stahmann et al. |
| 2004/0215262 A1 | 10/2004 | Ferek-Petric |
| 2004/0260348 A1 | 12/2004 | Bakken et al. |
| 2005/0043644 A1 | 2/2005 | Stahmann et al. |
| 2005/0043768 A1 | 2/2005 | Goode |
| 2005/0065554 A1 | 3/2005 | KenKnight et al. |
| 2005/0096705 A1 | 5/2005 | Pastore et al. |
| 2005/0137630 A1 | 6/2005 | Ding et al. |
| 2005/0177195 A1 | 8/2005 | Salo |
| 2006/0036290 A1 | 2/2006 | Hopper et al. |
| 2006/0074189 A1 | 4/2006 | Gammie |
| 2006/0122679 A1 | 6/2006 | Wengreen et al. |
| 2006/0224225 A1 | 10/2006 | Ransbury et al. |
| 2006/0287684 A1 | 12/2006 | Baynham et al. |
| 2008/0114408 A1 | 5/2008 | Shuros et al. |
| 2008/0119904 A1 | 5/2008 | Salo et al. |
| 2009/0082823 A1 | 3/2009 | Shuros et al. |

FOREIGN PATENT DOCUMENTS

| | | | |
|---|---|---|---|
| WO | WO-0130443 A1 | 5/2001 |
| WO | WO-0176689 A2 | 10/2001 |
| WO | WO-02087694 A1 | 11/2002 |
| WO | WO-2006069322 A2 | 6/2006 |
| WO | WO-2006069323 A1 | 6/2006 |
| WO | WO-2006074189 A1 | 7/2006 |
| WO | WO-2008063470 A1 | 5/2008 |
| WO | WO-2008063536 A1 | 5/2008 |
| WO | WO-2008079370 A1 | 7/2008 |

OTHER PUBLICATIONS

"U.S. Appl. No. 11/559,131, Final Office Action mailed Jun. 23, 2010", 13 pgs.

"U.S. Appl. No. 11/559,131, Final Office Action mailed Jul. 10, 2009", 10 pgs.

"U.S. Appl. No. 11/559,131, Non Final Office Action mailed Dec. 23, 2010", 12 pgs.

"U.S. Appl. No. 11/559,131, Non-Final Office Action mailed Dec. 31, 2009", 11 pgs.

"U.S. Appl. No. 11/559,131, Response filed Mar. 31, 2010 to Non Final Office Action mailed Dec. 31, 2009", 8 pgs.

"U.S. Appl. No. 11/559,131, Response filed Sep. 23, 2010 to Final Office Action mailed Jun. 23, 2010", 8 pgs.

"U.S. Appl. No. 11/559,131, Response filed Oct. 13, 2009 to Final Office Action mailed Jul. 10, 2009", 9 pgs.

"U.S. Appl. No. 11/561,049, Final Office Action mailed Jul. 12, 2010", 15 pgs.

"U.S. Appl. No. 11/561,049, Final Office Action mailed Jul. 13, 2009", 12 pgs.

"U.S. Appl. No. 11/561,049, Non-Final Office Action mailed Dec. 31, 2009", 12 pgs.

"U.S. Appl. No. 11/561,049, Notice of Allowance mailed Dec. 29, 2010", 6 pgs.

"U.S. Appl. No. 11/561,049, Response filed Mar. 31, 2010 to Non Final Office Action mailed Dec. 31, 2009", 10 pgs.

"U.S. Appl. No. 11/561,049, Response filed Nov. 12, 2010 to Final Office Action mailed Jul. 12, 2010", 11 pgs.

"U.S. Appl. No. 11/561,049, Response filed Nov. 13, 2009 to Final Office Action mailed Jul. 13, 2009", 9 pgs.

"U.S. Appl. No. 11/615,383, Final Office Action mailed Mar. 12, 2010", 14 pgs.

"U.S. Appl. No. 11/615,383, Non-Final Office Action mailed Feb. 5, 2009", 13 pgs.

"U.S. Appl. No. 11/615,383, Notice of Allowance mailed May 11, 2011", 5 pgs.

"U.S. Appl. No. 11/615,383, Notice of Allowance mailed Dec. 30, 2010", 7 pgs.

"U.S. Appl. No. 11/615,383, Notice of Non-Compliant Amendment mailed Sep. 18, 2009", 3 pgs.

"U.S. Appl. No. 11/615,383, Response filed May 7, 2009 to Non Final Office Action mailed Feb. 5, 2009", 7 pgs.

"U.S. Appl. No. 11/615,383, Response filed Aug. 12, 2010 to Final Office Action mailed Mar. 12, 2010", 9 pgs.

"U.S. Appl. No. 11/615,383, Response filed Oct. 19, 2009 to Notice of Non-Compliant Amendment mailed Oct. 19, 2009", 7 pgs.

"U.S. Appl. No. 11/903,758 Final Office Action mailed Jul. 20, 2010", 15 pgs.

"U.S. Appl. No. 11/903,758, Non-Final Office Action mailed Dec. 21, 2009", 10 pgs.

"U.S. Appl. No. 11/903,758, Response filed Apr. 21, 2010 to Non Final Office Action mailed Dec. 21, 2009", 10 pgs.

"U.S. Appl. No. 11/903,758, Response filed Oct. 20, 2010 to Final Office Action mailed Jul. 20, 2010", 11 pgs.

"Australian Application Serial No. 2007322056, First Examiner Report mailed Sep. 6, 2010", 3 pgs.

"Australian Application Serial No. 2007322172, First Examiner Report mailed Dec. 1, 2010", 4 pgs.

"Australian Application Serial No. 2007338688, First Examiner Report mailed May 27, 2010", 4 Pgs.

"European Application Serial No. 07853460.9, Office Action mailed Aug. 6, 2010", 5 pgs.

"European Application Serial No. 07853460.9, Response filed Jan. 25, 2011 to Office Action mailed Aug. 6, 2010", 9 pgs.

"European Application Serial No. 07861949.1, Office Action mailed Jun. 2, 2010", 3 pgs.

"European Application Serial No. 07861949.1, Response filed Dec. 9, 2010 to Office Action mailed Jun. 2, 2010", 11 pgs.

"European Application Serial No. 07862054.9, Office Action mailed Sep. 18, 2009", 3 pgs.

"European Application Serial No. 07862054.9, Office Action mailed Dec. 3, 2010", 6 pgs.

"International Application Serial No. PCT/US2007/023996, International Search Report mailed Apr. 1, 2008", 4 pgs.

"International Application Serial No. PCT/US2007/023996, Written Opinion mailed Apr. 1, 2008", 6 pgs.

"International Application Serial No. PCT/US2007/026235, International Search Report mailed Apr. 7, 2008", 4 pgs.

"International Application Serial No. PCT/US2007/026235, Written Opinion mailed Apr. 7, 2008", 8 pgs.

"PCT Application Serial No. PCT/US2007/023769, International Search Report mailed Mar. 20, 2008", 4 pgs.

"PCT Application Serial No. PCT/US2007/023769, Written Opinion mailed Mar. 20, 2008", 8 pgs.

Adamopoulos, S., "Effects of pulsed beta-stimulant therapy on beta-adrenoceptors and chronotropic responsiveness in chronic heart failure.", Lancet, 345(8946), (Feb. 11, 1995), 344-9.

Coats, A. J., "Controlled trial of physical training in chronic heart failure. Exercise performance, hemodynamics, ventilation, and autonomic function.", Circulation, 85(6), (Jun. 1992), 2119-31.

Goldsmith, R., et al., "Exercise and autonomic function.", Coron Artery Dis, 11(2), (Mar. 2000), 129-35.

Koizumi, T., "Improvement of left ventricular dysfunction during exercise by walking in patients with successful percutaneous coronary intervention for acute myocardial infarction.", Circ J., 67(3), (Mar. 2003), 233-7.

Leier, C. V., "Drug-induced conditioning in congestive heart failure.", Circulation, 65(7), (Jun. 1982), 1382-7.

Liang, C., "Conditioning effects of chronic infusions of dobutamine. Comparison with exercise training.", Journal of Clinical Investigation, 64(2), (Aug. 1979), 613-9.

Myers, J., "Exercise training and myocardial remodeling in patients with reduced ventricular function: one-year follow-up with magnetic resonance imaging", Am Heart J., 139(2), (Feb. 2000), 252-61.

Nakamoto, T., et al., "Beat-to-beat modulation of atrioventricular conduction during dynamic exercise in humans.", Jpn J Physiol., 55(1), (Feb. 2005), 37-51.

Nakamoto, T., et al., "Variability of ventricular excitation interval does not reflect fluctuation in atrial excitation interval during exercise in humans: AV nodal function as stabilizer.", J Physiol Sci., 56(1), (Feb. 2006), 67-77.

Prinzen, Frits W, "Mapping of regional myocardial strain and work during ventricular pacing: experimental study using magnetic resonance imaging tagging", Journal of the American College of Cardiology, 33(6), (May 1999), 1735-1742.

Salo, R., "Method and Device for Treating Myocardial Ischemia", U.S. Appl. No. 11/561,049, filed Nov. 17, 2006.

Sathaye, A. S., et al., "Post-MI Pacing With Autocapture Function", U.S. Appl. No. 11/427,517, filied Jun. 29, 2006, 20 pgs.

Shuros, A. C., et al., "Method and Device for Simulated Exercise", U.S. Appl. No. 11/559,131, filed Nov. 13, 2006, 32 pgs.

Vegh, A., et al., "Exercise and Delayed Preconditioning in the Protection of the Heart Aganist Ventricular Arrhythmias: Crucial Role of Nitric Oxide", Myocardial Ischemia and Preconditioning. Springer ISBN 1402071957, (2003), 423-429.

Weaver, et al., "Pulmonary Edema Associated with Hyperbaric Oxygen Therapy", Chest, 120, (2001), 1407-1409.

Wolfel, E. E., "Marathoners or couch potatoes: what is the role of exercise in the management of heart failure?", Current Heart Failure Reports, 2(1), (Mar. 2005), 25-34.

REDUCTION OF AV DELAY FOR TREATMENT OF CARDIAC DISEASE

CLAIM OF PRIORITY

This application is a continuation of U.S. patent application Ser. No. 11/615,383, filed on Dec. 22, 2007, now issued as U.S. Pat. No. 8,019,416 and hereby incorporated by reference herein in its entirety. U.S. patent application Ser. No. 11/615,383 is a continuation-in-part of U.S. patent application Ser. Nos. 11/561,049, filed on Nov. 17, 2006, now issued as U.S. Pat. Nos. 7,941,216 and 11/559,131, filed on Nov. 13, 2006, the disclosures of which are hereby incorporated by reference.

FIELD OF THE INVENTION

This invention pertains to apparatus and methods for the treatment of heart disease and to devices providing electrostimulation to the heart such as cardiac pacemakers.

BACKGROUND

Cardiac rhythm management devices are implantable devices that provide electrical stimulation to selected chambers of the heart in order to treat disorders of cardiac rhythm and include pacemakers and implantable cardioverter/defibrillators. A pacemaker is a cardiac rhythm management device that paces the heart with timed pacing pulses. (As the term is used herein, a pacemaker is any cardiac rhythm management device with a pacing functionality, regardless of any other functions it may perform such as delivery of cardioversion/defibrillation shocks.) The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Pacing therapy may also be applied in order to treat cardiac rhythms that are too fast, termed anti-tachycardia pacing.

Also included within the concept of cardiac rhythm is the manner and degree to which the heart chambers contract during a cardiac cycle to result in the efficient pumping of blood. For example, the heart pumps more effectively when the chambers contract in a coordinated manner. The heart has specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways, such as bundle branch blocks, can thus suffer compromised cardiac output. Heart failure (HF) refers to a clinical syndrome in which an abnormality of cardiac function causes a below normal cardiac output that can fall below a level adequate to meet the metabolic demand of peripheral tissues. Heart failure can be due to a variety of etiologies with ischemic heart disease being the most common (e.g., HF resulting from a myocardial infarction or MI). Intraventricular and/or interventricular conduction defects are commonly found in HF patients. In order to treat these problems, cardiac rhythm management devices have been developed which provide electrical pacing stimulation to one or more heart chambers in an attempt to improve the coordination of atrial and/or ventricular contractions, termed cardiac resynchronization therapy (CRT). Currently, a most common form of CRT is biventricular pacing in which paces are delivered to both ventricles in a manner that synchronizes their contractions.

Bradycardia pacing and CRT are delivered using bradycardia pacing modes that determine how the pacing pulses are delivered in response to sensed cardiac events and lapsed time intervals. Such modes may either be single-chamber pacing, where either an atrium or a ventricle is paced, or dual-chamber pacing in which both an atrium and a ventricle are paced. Particular modes may be designated by a letter code of three positions where each letter in the code refers to a specific function of the pacemaker. The first letter refers to which heart chambers are paced and which may be an A (for atrium), a V (for ventricle), D (for both chambers), or O (for none). (As the code is used herein, when an atrium or ventricle designated as paced, this may also refer to multiple site pacing such as biatrial or biventricular pacing.) The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Additional sensing of physiological data allows some pacemakers to change the rate at which they pace the heart in accordance with some parameter correlated to metabolic demand. Such pacing is called rate-adaptive pacing and is designated by a fourth letter added to the three-letter code, R. Modern pacemakers are typically programmable so that they can operate in any mode which the physical configuration of the device will allow.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia or delivering CRT today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

During normal physiological beats, atrial contractions augment the diastolic filling of the ventricles. When the ventricles are paced upon expiration of a ventricular escape without regard to atrial activity such as in a VVI mode, the normal synchrony between atrial and ventricular contractions that occurs in intrinsic physiological beats is lost. Such atrioventricular dyssynchrony can compromise cardiac output to a clinically significant extent, sometimes referred to as pacemaker syndrome. It is therefore normally preferable to employ atrial triggered pacing modes that attempt to maintain the physiological synchrony between atrial and ventricular contractions.

In atrial triggered modes (e.g., VDD and DDD modes), another ventricular escape interval is defined between atrial and ventricular events, referred to as the atrio-ventricular delay interval or AVD. The atrio-ventricular interval is triggered by an atrial sense or pace and stopped by a ventricular sense or pace. A ventricular pacing pulse is delivered upon expiration of the atrio-ventricular interval if no ventricular sense occurs before. The value of the atrio-ventricular interval for optimal preloading of the ventricles will vary with heart rate and in a manner that differs from patient to patient. If a patient has a physiologically normal atrial rhythm, ventricular pacing triggered by atrial senses also allows the ventricular pacing rate to be responsive to the metabolic needs of the body. If the atrial rhythm is too slow, the device can be configured to pace the atria on an inhibited demand basis such as in DDD mode which may include rate-adaptive pacing. An atrial escape interval is then defined as the maximum time interval in which an atrial sense must be detected after a ventricular sense or stimulus before an atrial stimulus will be delivered. The lower rate limit interval is then the sum of the atrial escape interval and the atrio-ventricular interval.

In a patient with normal AV conduction (i.e., no degree of AV block) and normal ventricular function, the optimum AVD that maximizes cardiac output will usually correspond closely with the intrinsic atrio-ventricular interval. When such an AVD is used for bradycardia pacing of the ventricles, the ventricular pace is thus delivered close to the time that the ventricles become excited due to intrinsic AV conduction. Similarly, an optimum AVD for resynchronizing the ventricles with biventricular pacing in a patient with intact AV conduction will usually involve pre-exciting the ventricle having the conduction deficit with an AVD that causes that ventricle to contract at roughly the same time that the contralateral ventricle contracts due to intrinsic AV conduction. As described below, however, in patients with compromised ventricular function, it may be advantageous at times to employ an AVD for ventricular pacing that is much shorter than the intrinsic atrio-ventricular interval.

DETAILED DESCRIPTION

As described below, an implantable pacing device for delivering ventricular pacing may be configured to intermittently reduce the AVD interval for beneficial effect in patients with compromised ventricular function (e.g., HF patients and post-MI patients). The AVD interval may be reduced, referred to herein as an AVD reduction or AVDR mode, by shortening the AVD in an atrial triggered ventricular pacing mode or by switching to a non-atrial triggered ventricular pacing mode (e.g., VVI) and delivering paces at a rate above the intrinsic rate. Reduction of the AVD primarily results in two things: a reduction in the extent of ventricular pre-loading by the atria and a relatively asynchronous ventricular contraction brought about by the ventricles being excited from one or more ventricular pacing sites with little or no accompanying ventricular excitation via intrinsic AV conduction. The physiological effects of AVD reduction may be either positive or negative on cardiac output, depending upon the individual patient.

Some patients may exhibit either an increased or relatively unchanged cardiac output when the AVD is reduced. Such patients, who may be referred to as positive responders, include HF patients who are over-compensated with an increased ventricular preload. If the AVD is either eliminated or severely reduced in these patients, the ventricles then receive very little preloading from the atria. The reduction in ventricular pre-load may then actually improve ventricular function and increase cardiac output. Another group of positive responders include patients who exhibit an increased ventricular pressure afterload from aortic pressure reflections due to atherosclerotic stiffening of the aorta. In these patients, the ventricles are subjected to an increased stress and energy expenditure that does not contribute to increasing cardiac output. Reduction of the atrial preload by reducing or eliminating the AVD has been found to reduce the aortic pressure reflections in these patients and result in either an increased or relatively unchanged cardiac output. Delivery of ventricular pacing in an AVDR mode to positive responders thus increases cardiac output and/or reduces ventricular wall stress and energy expenditure during systole without unduly compromising cardiac output. The AVDR mode may be controlled by feedback to prevent the pulmonary congestion that may occur as blood is forced back into the lungs when atrial preloading is reduced. Such feedback may be provided by a sensor for detecting pulmonary edema, by sensor for measuring pulmonary artery pressure, or by a switch that may be actuated by the patient when symptoms of pulmonary edema are present. The AVDR mode may also be controlled so as to be ceased or reduced in frequency when the patient is in a supine position as detected by a posture sensor.

Another group of patients, referred to as negative responders, respond to AVD reduction with a relatively compromised cardiac output due to the reduction in atrial preloading and/or the relatively asynchronous and inefficient ventricular contraction resulting from a pace without intrinsic excitation from AV conduction. It has long been known that the heart muscle responds favorably to exercise so as to result in greater pumping efficacy. Studies have shown that HF and post-MI patients can improve their cardiac function and prognosis with regular periods of exercise. Many HF and post-MI patients, however, are either debilitated and cannot exercise or do not tolerate exercise well enough to exercise effectively. Delivering ventricular pacing with a reduced AVD to a negatively responding patient produces a relatively asynchronous and inefficient contraction that simulates the stress effects of exercise on the heart. The optimum value of a shortened AVD for producing an asynchronous contraction may vary from patient to patient but would typically be between 35-80 percent of the intrinsic atrio-ventricular interval. A particular patient could also be both a positive or negative responder depending upon the extent to which the AVD is reduced.

Ventricular pacing in an AVDR mode may delivered on an intermittent basis as controlled by specified entry and exit conditions that could include lapsed time intervals, detection of pulmonary edema, exertion level (e.g., as measured by intrinsic heart rate, activity level, or minute ventilation), patient posture, cardiac output, and blood pressure. The manner in which entry and exit into the AVDR mode is controlled will depend upon whether the effect of the AVDR mode is to improve cardiac function in a positive responder (by increasing cardiac output and/or cardiac efficiency) or to simulate the effects of exercise in a negative responder. Also, the manner in which the AVDR mode is implemented may depend upon whether the intended effect is to improve cardiac function or to simulate exercise. For example, cardiac function may be optimally improved in a positive responder by drastically shortening or even eliminating the AVD during ventricular pacing. Simulating exercise in a negative responder, on the other hand, may be best accomplished with an AVD reduced to such an extent that asynchronous contractions are produced but without severely reducing atrial preloading (e.g., with an AVD that is between 35-80 percent of the intrinsic atrio-ventricular interval). A more detailed description of these techniques is given below after a description of an exemplary cardiac device.

1. Exemplary Cardiac Device

Figure 1:
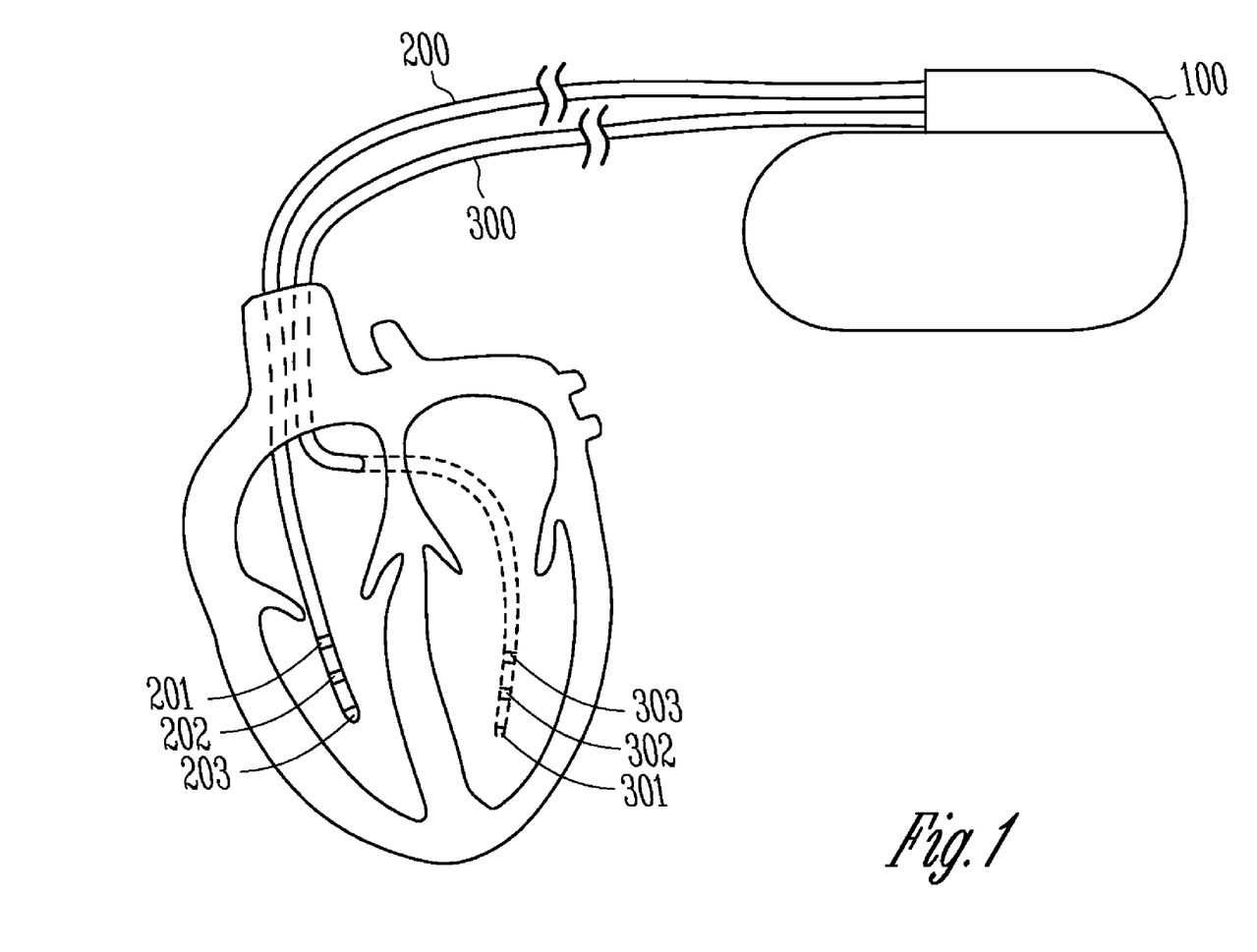
FIG. 1 illustrates the physical configuration of an exemplary pacing device.

FIG. 1 shows an implantable cardiac device 100 for delivering pacing therapy. Implantable pacing devices are typically placed subcutaneously or submuscularly in a patient's chest with leads threaded intravenously into the heart to connect the device to electrodes disposed within a heart chamber that are used for sensing and/or pacing of the chamber. Electrodes may also be positioned on the epicardium by various means. A programmable electronic controller causes the pacing pulses to be output in response to lapsed time intervals and/or sensed electrical activity (i.e., intrinsic heart beats not as a result of a pacing pulse). The device senses intrinsic cardiac electrical activity through one or more sensing channels, each of which incorporates one or more of the electrodes. In order to excite myocardial tissue in the absence of an intrinsic beat, pacing pulses with energy above a certain threshold are delivered to one or more pacing sites through one or more pacing channels, each of which incorporates one or more of the electrodes. FIG. 1 shows the exemplary device having two leads 200 and 300, each of which is a multi-polar (i.e., multi-electrode) lead having electrodes 201-203 and 301-303, respectively. The electrodes 201-203 are disposed in the right ventricle in order to excite or sense right ventricular or septal regions, while the electrodes 301-303 are disposed in the coronary sinus in order to excite or sense regions of the left ventricle. Other embodiments may use any number of electrodes in the form of unipolar and/or multi-polar leads in order to excite different myocardial sites. As explained below, once the device and leads are implanted, the pacing and/or sensing channels of the device may be configured with selected ones of the multiple electrodes in order to selectively pace or sense a particular myocardial site(s).

Figure 2:
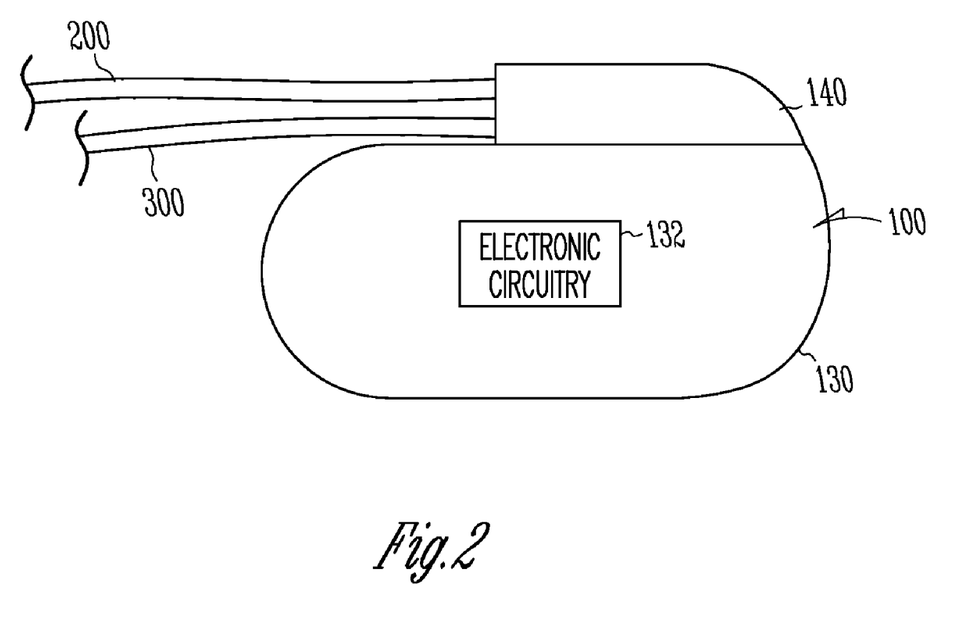
FIG. 2 shows the components of an exemplary device.

FIG. 2 shows the components of the implantable device 100 in more detail. The implantable device 100 includes a hermetically sealed housing 130 that is placed subcutaneously or submuscularly in a patient's chest. The housing 130 may be formed from a conductive metal, such as titanium, and may serve as an electrode for delivering electrical stimulation or sensing in a unipolar configuration. A header 140, which may be formed of an insulating material, is mounted on the housing 130 for receiving leads 200 and 300 which may be then electrically connected to pulse generation circuitry and/or sensing circuitry. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device.

Figure 3:
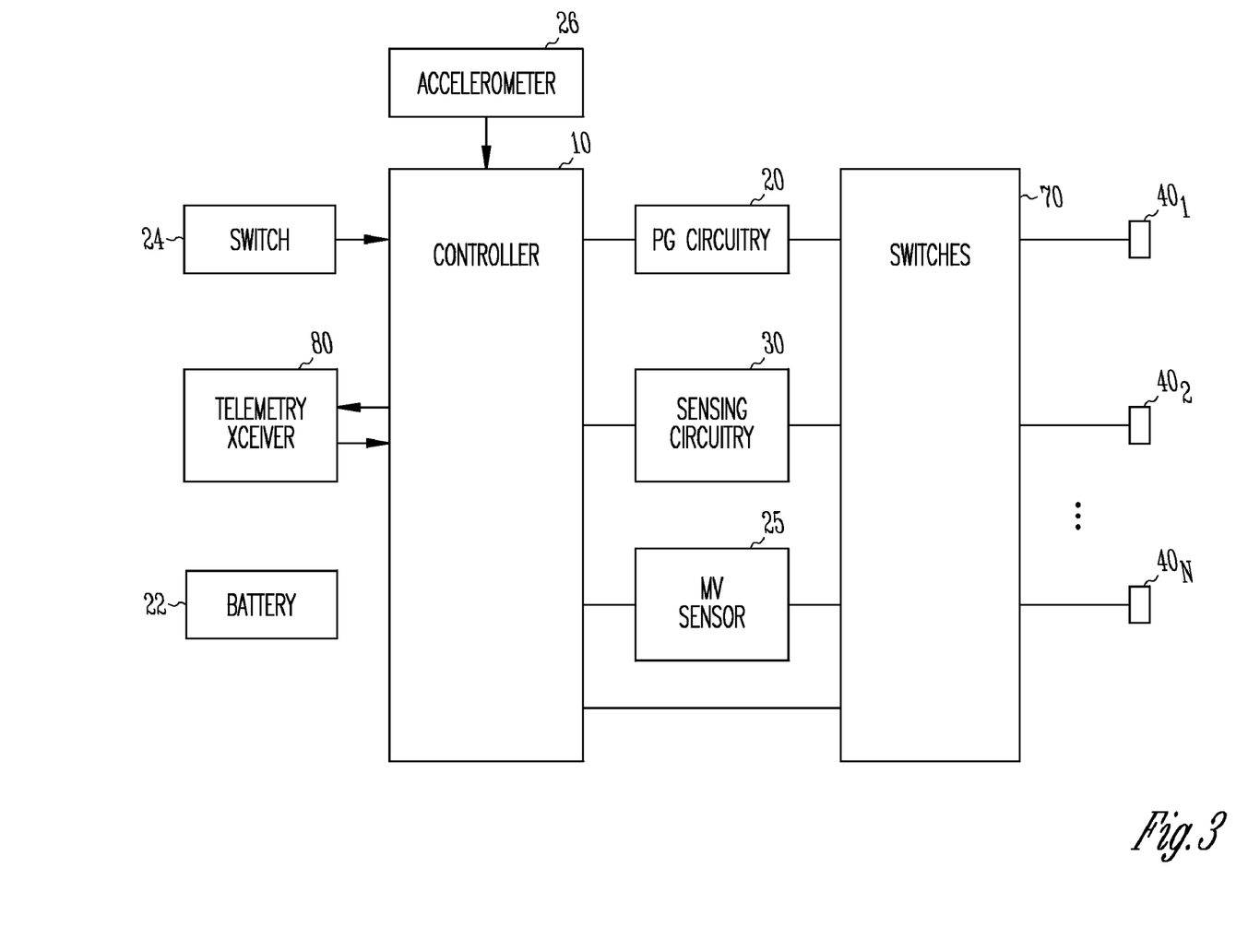
FIG. 3 is a block diagram of the electronic circuitry of an exemplary device.

FIG. 3 shows a system diagram of the electronic circuitry 132. A battery 22 supplies power to the circuitry. The controller 10 controls the overall operation of the device in accordance with programmed instructions and/or circuit configurations. The controller may be implemented as a microprocessor-based controller and include a microprocessor and memory for data and program storage, implemented with dedicated hardware components such as ASICs (e.g., finite state machines), or implemented as a combination thereof. The controller also includes timing circuitry such as external clocks for implementing timers used to measure lapsed intervals and schedule events. As the term is used herein, the programming of the controller refers to either code executed by a microprocessor or to specific configurations of hardware components for performing particular functions. Interfaced to the controller are sensing circuitry 30 and pulse generation circuitry 20 by which the controller interprets sensing signals and controls the delivery of paces in accordance with a pacing mode. The controller is capable of operating the device in a number of programmed pacing modes which define how pulses are output in response to sensed events and expiration of time intervals. The controller also implements timers derived from external clock signals in order to keep track of time and implement real-time operations such as scheduled AVDR mode pacing.

The sensing circuitry 30 receives atrial and/or ventricular electrogram signals from sensing electrodes and includes sensing amplifiers, analog-to-digital converters for digitizing sensing signal inputs from the sensing amplifiers, and registers that can be written to for adjusting the gain and threshold values of the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively.

The pulse generation circuitry 20 delivers pacing pulses to pacing electrodes disposed in the heart and includes capacitive discharge or current source pulse generators, registers for controlling the pulse generators, and registers for adjusting pacing parameters such as pulse energy (e.g., pulse amplitude and width). The device allows adjustment of the pacing pulse energy in order to ensure capture of myocardial tissue (i.e., initiating of a propagating action potential) by a pacing pulse. The pulse generation circuitry may also include a shocking pulse generator for delivering a defibrillation/cardioversion shock via a shock electrode upon detection of a tachyarrhythmia.

A telemetry transceiver 80 is interfaced to the controller which enables the controller to communicate with an external device such as an external programmer and/or a remote monitoring unit. An external programmer is a computerized device with an associated display and input means that can interrogate the pacemaker and receive stored data as well as directly adjust the operating parameters of the pacemaker. The external device may also be a remote monitoring unit that may be interfaced to a patient management network enabling the implantable device to transmit data and alarm messages to clinical personnel over the network as well as be programmed remotely. The network connection between the external device and the patient management network may be implemented by, for example, an internet connection, over a phone line, or via a cellular wireless link. A switch 24 is also shown as interfaced to the controller in this embodiment to allow the patient to signal certain conditions or events to the implantable device. In different embodiments, the switch 24 may be actuated magnetically, tactilely, or via telemetry such as by a hand-held communicator. The controller may be programmed to use actuation of the switch 24 to control the delivery of AVDR mode pacing.

A pacing channel is made up of a pulse generator connected to an electrode, while a sensing channel is made up of a sense amplifier connected to an electrode. Shown in the figure are electrodes $40_1$ through $40_N$ where N is some integer. The electrodes may be on the same or different leads and are electrically connected to a MOS switch matrix 70. The switch matrix 70 is controlled by the controller and is used to switch selected electrodes to the input of a sense amplifier or to the output of a pulse generator in order to configure a sensing or pacing channel, respectively. The device may be equipped with any number of pulse generators, amplifiers, and electrodes that may be combined arbitrarily to form sensing or pacing channels. The device is therefore capable of delivering single-site or multiple site ventricular pacing for purposes of exercise simulation as well as conventional pacing. One or more pacing channels may also be configured, by appropriate lead placement and pulse energy/frequency settings, for delivering electrical stimulation to stimulate sympathetic and/or parasympathetic nerves. For example, a lead with a stimulation electrode may be placed in proximity to the vagus nerve in order to stimulate that nerve and increase parasympathetic activity. The switch matrix 70 also allows selected ones of the available implanted electrodes to be incorporated into sensing and/or pacing channels in either unipolar or bipolar configurations. A bipolar sensing or pacing configuration refers to the sensing of a potential or output of a pacing pulse between two closely spaced electrodes, where the two electrodes are usually on the same lead (e.g., a ring and tip electrode of a bipolar lead or two selected electrodes of a multi-polar lead). A unipolar sensing or pacing configuration is where the potential sensed or the pacing pulse output by an electrode is referenced to the conductive device housing or another distant electrode.

The device may also include one or more physiological sensing modalities for use in controlling pacing and/or the initiation/cessation of the AVDR mode. An accelerometer 26 enables the controller to adapt the pacing rate in accordance with changes in the patient's physical activity. In order to detect patient posture for purposes of controlling AVDR mode pacing, the accelerometer 26 may be a multi-axis accelerometer. An impedance sensor 25 may be configured with electrodes for measuring minute ventilation for use in rate adaptive pacing and/or cardiac output for use in controlling the AVDR mode. The impedance sensor 25 may also be configured to detect pulmonary edema by measurement of trans-pulmonary impedance. The device may also include a pressure sensor that may be used, for example, to measure pressure in the pulmonary artery.

2. Reduction of AVD to Improve Cardiac Function

Inadequate pumping of blood into the arterial system by the heart is sometimes referred to as "forward failure," with "backward failure" referring to the resulting elevated pressures in the lungs and systemic veins which lead to congestion. Backward failure is the natural consequence of forward failure as blood in the pulmonary and venous systems fails to be pumped out. Forward failure can be caused by impaired contractility of the ventricles due, for example, to coronary artery disease, or by an increased afterload (i.e., the forces resisting ejection of blood) due to, for example, systemic hypertension or valvular dysfunction. One physiological compensatory mechanism that acts to increase cardiac output in this situation is due to backward failure which increases the diastolic filling pressure of the ventricles and thereby increases the preload (i.e., the degree to which the ventricles are stretched by the volume of blood in the ventricles at the end of diastole). An increase in preload causes an increase in stroke volume during systole, a phenomena known as the Frank-Starling principle, whereby increases in myocardial fiber lengthening during diastole results in greater contractile force being generated during systole. Thus, heart failure can be at least partially compensated by this mechanism but at the expense of possible pulmonary and/or systemic congestion.

Figure 4:
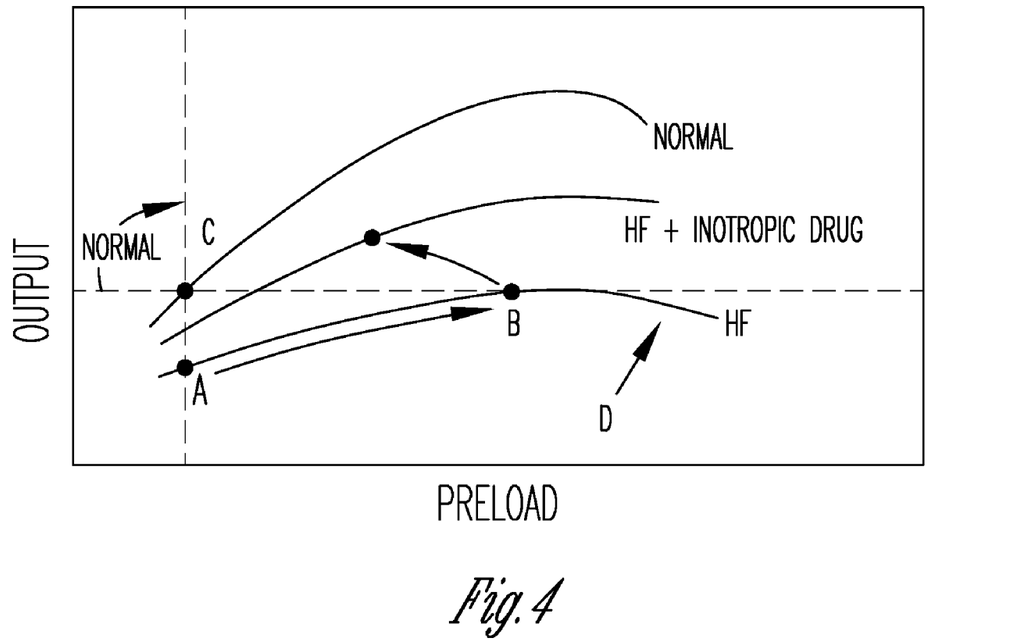
FIG. 4 illustrates a Starling curve that relates ventricular preload to cardiac output.

Compensation of heart failure by increasing ventricular preload is only effective in increasing cardiac output up to a certain extent, however, beyond which an increased preload may actually diminish cardiac output. FIG. 4 illustrates this situation by showing examples of two Starling curves, one for a normal subject and the other for an HF patient, that relate cardiac output to ventricular preload. Both curves show a positively sloping region where cardiac output increases with increasing preload and a negatively sloping region where further increases in preload cause a decrease in cardiac output. At the point labeled C on the normal curve, a normal or adequate cardiac output results from a particular amount of preload. At that same preload for an HF patient, however, an inadequate cardiac output results, shown as point A on the HF curve. This situation may be compensated for by increasing the preload to increase cardiac output to an adequate level, shown as point B on the HF curve. Any further increases in preload, however, moves to negatively sloping region of the Starling curve labeled D and causes a diminution in cardiac output. HF patients who are operating in a negatively sloping region of their Starling curve may be said to be overcompensated, and such patients may be identified by clinical hemodynamic testing. The cardiac function of these patients may be improved by reducing or eliminating the contribution of atrial contractions to ventricular preload with AVDR pacing.

Figure 5:
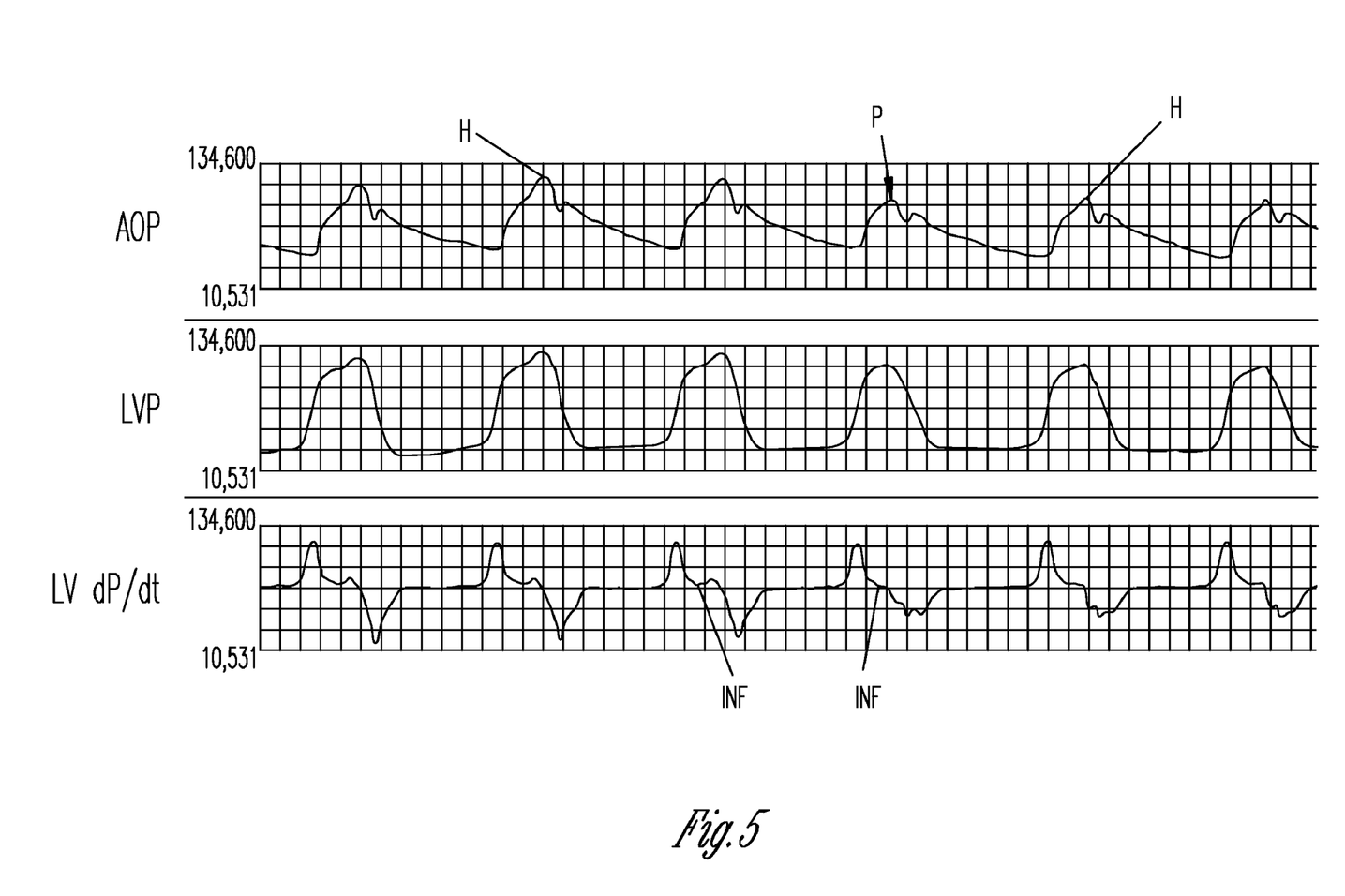
FIG. 5 illustrates the effects of reducing ventricular preload on aortic reflections.

Another situation in which the atrial contribution to ventricular preload may be deleterious is when aortic reflections, secondary to arterial stiffening from atherosclerosis, occur. In this case the ventricle is also unnecessarily loaded with additional pressure, with no benefit in forward flow. The additional pressure caused by these reflections is not of an insignificant magnitude (e.g., 3 to 15 mmHg). This problem of mechanical-impedance mismatch between the pump and its load, a product of normal aging and genetic disposition to endothelial disease, has been well described in the literature as a precursor to hypertension and heart failure. The mechanism of reflections involves the reduced capacitance of the arterial load, a result of a stiffer aorta and arterial tree. It has been found that these aortic reflections be significantly reduced by ventricular pacing with short AV delays as illustrated by FIG. 5 for an example patient. In FIG. 5, three pressure channels are shown: aortic pressure AOP, left ventricular pressure LVP, and the rate of left ventricular pressure change LV dP/dt. The patient shows aortic reflections, evident as "humps" labeled H in the top of the AOP pulse signal. The dP/dt signal also shows the reflection's inflection point clearly, as small humps after the main systolic phase labeled as INF. It is seen that when pacing with a short AVD is initiated at point P, the aortic reflections evident in the AOP and dP/dt channels are reduced significantly. Such aortic reflections are wasteful, and eliminating them causes no loss in output, but does result in less loading and more efficient pumping by the ventricle. Note also that the maximum value of dP/dt is unaffected. Thus, in this pathological condition, an implantable pacing device could intervene therapeutically in patients identified with vascular stiffening to reduce the loading of the ventricle by pacing in an AVDR mode with a short AVD to eliminate the needless reflections.

Patients identified as either overcompensated with either high diastolic filling pressures or as having aortic reflections may thus be regarded as positive responders to AVDR pacing. That is, AVDR pacing in these patients results in improved cardiac function manifested as increased cardiac output and/or cardiac pumping efficiency. AVDR pacing reduces or eliminates the atrial contribution to ventricular preload, implemented either by pacing with a very short or zero AV delay, or by pacing in a VVI mode just above the normal sinus rate. It is well known, however, that AV dissociation in dual chamber pacing can cause lung edema and the so called "pacemaker syndrome" malaise. The reason for this additional congestion is the backing of atrial pressure into the lungs, when the atria contract against a closed mitral valve. AVDR pacing, by eliminating AV synchrony, may have the same risk. Certain HF patients with good lymphatics, however, may be relatively immune to this risk, much in the same way that some HF patients do very well despite high wedge pressures. In these patients, AVDR pacing may be delivered by an implantable device on a more or less chronic basis. In patients who do not tolerate AV dyssynchrony well, on the other hand AVDR pacing therapy may be delivered intermittently with some sort of closed loop feedback control of the AVDR mode. Such feedback control may be provided by a sensor incorporated into the pacing device for pulmonary congestion detection (e.g. by measuring thoracic impedance or pulmonary artery pressure) or may be provided by a patient-operated hand-held device or other type of switch that the patient would operate to turn on or off the AVDR mode in accordance their own subjective symptoms. A postural sensor control could also be included so that the AVDR mode would be decreased in extent and/or frequency when the patient is determined to be in a supine position which is more likely to cause edema. Feedback control could also be used to increase the extent and/or frequency of the AVDR mode when it is determined that increased cardiac output is most needed such as during periods of exertion as determined from activity level, minute ventilation, or intrinsic heart rate.

3. Reduction of AVD to Simulate Exercise

Clinical studies have shown that HF and post-MI patients who follow a regular (e.g. 20 min/day, 3 times a week) exercise regimen have symptomatic improvement compared to those who are sedentary. However, not all HF and post-MI patients can exercise due to their cardiac disease or other debilitating conditions. As explained below, pacing therapy may be designed to mimic exercise in order to provide protection from heart failure development and/or attenuation/reversal of cardiac disease progression.

When cardiac output is insufficient to meet the increased metabolic demand, the body responds to the situation with increased activity of the sympathetic nervous system that, among other things, increases heart rate, myocardial contractility, and blood volume. Although acutely beneficial, the long-term effects of increased sympathetic activity are deleterious and lead to ventricular remodeling such as described above. A characteristic feature of chronic cardiac disease is an abnormal autonomic tone with an attenuated level of parasympathetic activity relative to sympathetic activity. When the heart is stressed on a periodic short-term basis, however, such as occurs with regular exercise, the effect is beneficial on both myocardial function and autonomic tone, leading to an increased level of parasympathetic activity. In order to mimic the effects of exercise, pacing therapy can be delivered on a short-term basis in a manner that stresses the heart similar to exercise. Such pacing therapy is referred to herein as simulated exercise pacing. Simulated exercise pacing may generally involve pacing the heart in a manner that temporarily compromises cardiac output by producing relatively inefficient ventricular contractions and/or some degree of atrio-ventricular dyssynchrony such as described in co-pending U.S. patent application Ser. No. 11/559,131, filed on Nov. 13, 2006.

One way of delivering simulated exercise pacing is with an AVDR mode. As described earlier, reducing the AVD causes AV dyssynchrony that decreases the amount of ventricular preloading. In a negative responder, decreasing the ventricular preload decreases cardiac output, and the body may respond to this decrease in a manner similar to its response to exercise. Ventricular pacing with a reduced AVD also causes a relatively asynchronous contraction that can decrease cardiac output to mimic the effects of exercise. The mechanism behind this effect is that when the ventricles are stimulated to contract by a pacing pulse applied through an electrode located at a particular pacing site, the excitation spreads from the pacing site by conduction through the myocardium. This is different from the normal physiological situation, where the spread of excitation to the ventricles from the AV node makes use of the heart's specialized conduction system made up of Purkinje fibers which allows a rapid and synchronous excitation of the entire ventricular myocardium. The excitation resulting from a pacing pulse, on the other hand, produces a relatively asynchronous contraction due to the slower velocity at which the excitation is conducted from the pacing site to the rest of the myocardium. Regions of the myocardium located more distally from the pacing site are also excited later than regions proximal to the pacing site as compared with an intrinsic contraction and subjected to increased mechanical stress. This increased regional stress may elicit cellular changes in the myocardium similar to those caused by stress due to exercise.

As described above, AVDR pacing can be delivered to the heart in a way that mimics the beneficial effects of exercise. Chronic simulated exercise pacing, however, could overstress the heart in HF or post-MI patients and could be hazardous. Accordingly, it would ordinarily be preferable to deliver simulated exercise pacing on an intermittent basis. As described below, a pacing device may therefore be configured to switch from a normal operating mode to an AVDR mode according to some defined exit and entry conditions that cause intermittent operation in the AVDR mode. Such entry and exit conditions, for example, may define a schedule that specifies switching in response to lapsed time intervals and/or in response to one or more other types of conditions detectable by the device.

4. Implementation of Normal and AVDR Modes

Switching from a normal operating mode to the AVDR mode may be implemented in a number of ways. If the normal mode does not include delivery of pacing therapy, the AVDR mode may include delivery of ventricular pacing in an atrial triggered mode with a short AVD or delivery of ventricular pacing a non-atrial triggered mode (e.g., VVI) at a rate above the intrinsic rate. If the normal mode includes atrial triggered pacing with a specified AVD, the AVDR mode may include ventricular pacing in an atrial triggered mode using an AVD shorter than that used in the normal operating mode or a non-atrial triggered mode such as VVI. For purposes of specifying the AVD used in the AVDR mode, the device may be configured to measure the intrinsic atrio-ventricular interval and compute the AVD as a specified percentage thereof. The device may also be configured to measure the intrinsic sinus rate before switching to non-atrial triggered ventricular pacing in the AVDR mode and delivering pacing at some higher rate. Non-atrial triggered pacing in the AVDR mode may also be delivered in an overdrive pacing mode where the pacing rate is varied in a manner that attempts to avoid intrinsic beats. When some kind of pacing therapy is delivered in the normal operating mode and the device possesses multiple pacing channels with different pacing sites, the AVDR mode may involve using either the same or a different pacing channel for delivering ventricular pacing. The AVDR mode may also involve ventricular pacing at multiple sites and/or switching to different pacing sites during operation of the mode according to some defined schedule.

5. Conditional Entry and Exit into AVDR Mode

Figure 6:
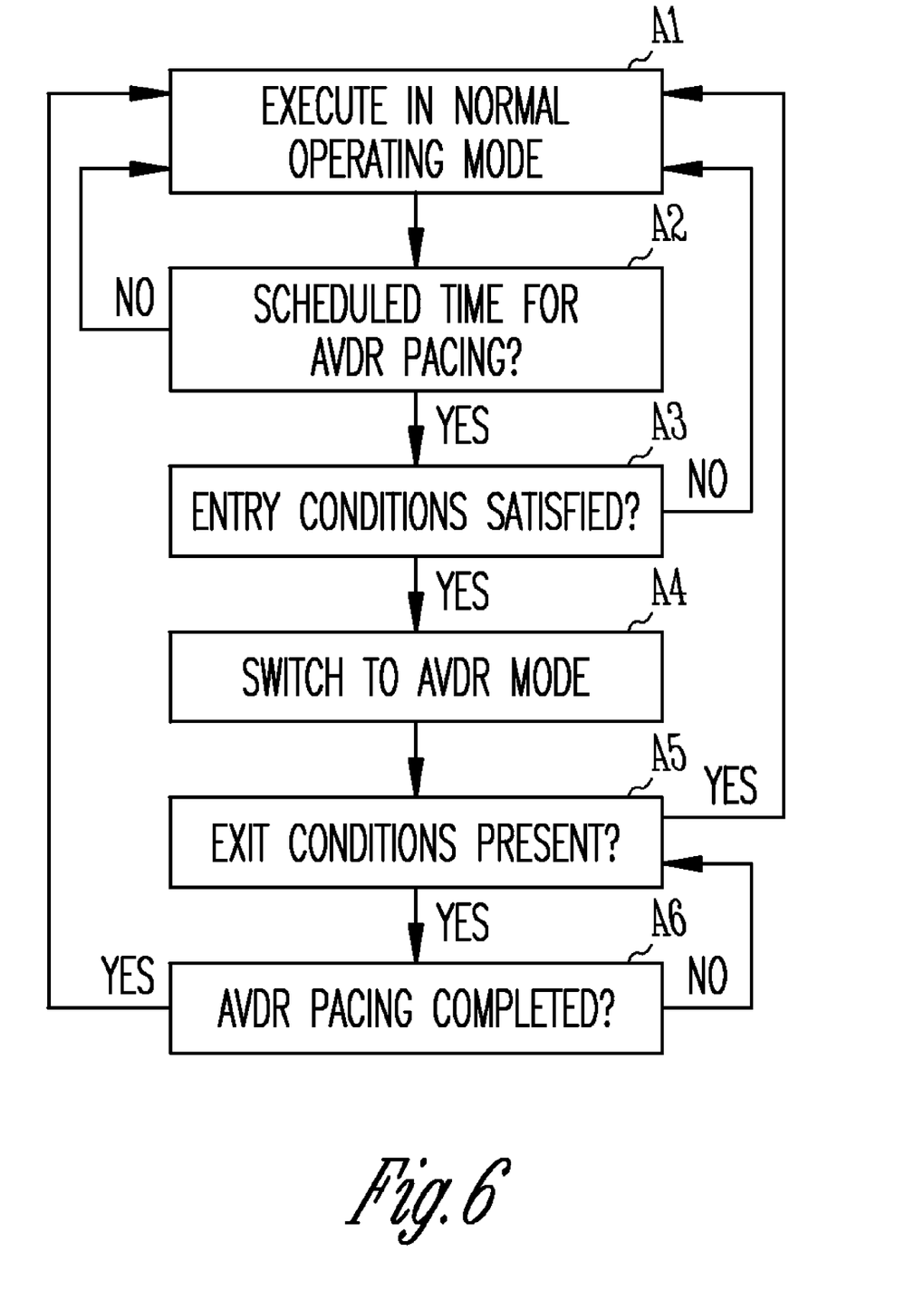
FIG. 6 illustrates an exemplary algorithm for controlling entry and exit into the AVDR mode.

The device may be configured to use one or more entry and/or exit conditions in controlling entry and/or exit into the AVDR. An entry or exit condition could be, for example, a lapsed time interval (e.g., specified time(s) of the day), actuation of a switch by the patient (e.g., a magnetically or tactilely actuated switch interfaced to the device controller), a command received via telemetry, detection or non-detection of a condition such as pulmonary edema or a supine posture, or a measured variable being within or out of a specified range. Examples of such measured variables include heart rate, activity level, minute ventilation, cardiac output, heart sounds, and blood pressure. Entry and/or exit conditions may also be composite conditions where a plurality of entry and/or exit conditions are logically ORed or ANDed together to determine whether a composite entry or entry condition is satisfied. FIG. 6 illustrates an exemplary algorithm executable by the device controller for controlling entry and exit into the AVDR mode. In this example, one of the entry conditions is a specified time of the day during which it is desired to delivery AVDR pacing if other entry conditions are met. As shown in the figure, the controller of the device is programmed to transition through a number of different states, designated as A1 through A6. At state A1, the device operates in its normal operating mode. At state A2, while continuing to operate in state A1, the device determines whether it should switch to the AVDR mode based upon a lapsed time interval or a triggering condition. Optionally, the device may also be configured to test for one or more particular entry conditions before switching to the simulated exercise mode as implemented by state A3. Examples of entry conditions that must be satisfied before the switch to the AVDR mode include a measured exertion level being within a specified entry range (where exertion level may be measured by, e.g., heart rate, activity level, or minute ventilation), non-detection of cardiac arrhythmias, non-detection of cardiac ischemia, receipt of a telemetry command, and actuation by the patient of a magnetically or tactilely actuated switch incorporated into the device that allows switching to the AVDR mode. At state A3, the device checks to see if the one or more entry conditions are satisfied and returns to state A1 if not. If the appropriate entry conditions are satisfied, the device switches to the AVDR mode at state A4. The AVDR mode supercedes the normal operating mode to the extent necessary to carry out the AVDR pacing but may allow certain functions performed in the normal operating mode to continue. Alternatively, the AVDR mode could be said to incorporate particular functions of the normal operating mode, which functions are modified if necessary to deliver the AVDR pacing. While executing in the AVDR mode, the device may be configured to monitor for one or more exit conditions which cause the device to revert to the normal operating mode. Such exit conditions could be the same or different from the entry conditions that must be satisfied before entering the AVDR mode. At state A5, while executing in the AVDR mode, the device monitors for the occurrence of one or more exit conditions such as a measured exertion level being outside a specified permissible range, a measured heart rate being outside a specified permissible range, presence of a cardiac arrhythmia, presence of cardiac ischemia, receipt of a telemetry command, and actuation by the patient of a magnetically or tactilely actuated switch incorporated into the device by the patient to stop delivery of AVDR pacing. If an exit condition occurs, the device returns to the normal operating mode at state A1. Otherwise, the device proceeds to state A6 and checks to see if the prescribed amount and/or duration of AVDR pacing have been delivered. If the specified amount or duration of AVDR pacing has been delivered, the device returns to state A1 and resumes the normal operating mode. Otherwise, the device loops back to state A5 to monitor for exit conditions.

The specification of particular entry and exit conditions for switching to the AVDR mode will depend upon the response of the patient to the particular kind of AVDR pacing being delivered. For example, in the case of a positive response to the AVDR pacing so that cardiac function is improved, the entry condition could be specified to be always satisfied so that AVDR pacing is delivered continuously or could be lapsed time interval to deliver AVDR pacing periodically. An entry condition could also be a measured exertion level being above some specified value. Exit conditions could then be detection of pulmonary edema, detection of a supine posture, and/or receipt of a command to cease AVDR pacing received via telemetry or actuation of a switch. In the case of a negative response to the AVDR pacing that simulates exercise, the entry condition(s) could be a lapsed time interval, measured cardiac output being above some specified value, and/or measured exertion level being below some specified value. For example, the device may be programmed to deliver AVDR pacing that simulates exercise for a prescribed amount of time per day (e.g. 30 min). The time when therapy delivery is started may be random (once per day at a random time), at a specific time each day, or triggered by a specific event (e.g. when the patient falls asleep, the patient wakes up, or the patient's exertion level falls below a certain threshold).

6. Exemplary Implementation Schemes

In an exemplary embodiment, the device is programmed to periodically (e.g., every 24 to 72 hours) switch to the AVDR mode for some specified period of time, referred to as the AVD reduction period or AVDRP (e.g., 15-60 minutes). If the device delivers some kind of therapy during its normal mode (e.g., for cardiac resynchronization therapy, remodeling control therapy, or bradycardia), the AVDR mode could be implemented as atrial triggered ventricular pacing (e.g., VDD or DDD) with a shorter AV delay than that used in the normal mode. If no pacing is delivered in the normal mode, the AVDR mode could be implemented as atrial triggered ventricular pacing with a specified short AV delay. If the device is equipped with an atrial lead and only a single implanted ventricular lead, the implanted ventricular site would be paced with the reduced AV delay for the entire AVDRP. If the device is equipped with electrodes implanted at multiple ventricular sites (e.g., as multiple leads or as one or multi-polar leads), all or some selected subset of the ventricular pacing sites could be paced during the AVDRP. The ventricular sites could also be rotated during the AVDRP according to a specified duty cycle. For example, if the device has electrodes implanted at two ventricular sites, the AVDR mode could be implemented as AVDR pacing delivered to a selected one of the sites for entire AVDRP, AVDR pacing delivered to one site for some percentage (e.g. 50%) of the AVDRP and switching to the other site for remaining portion of the AVDRP, or AVDR pacing delivered to both ventricular sites for each paced cycle (either simultaneously or with offset between the two sites) during the entire AVDRP. Similarly, if device has more than two ventricular leads or more than two ventricular pacing sites (e.g. quadripolar lead), AVDR pacing could be delivered to a single selected site for the entire AVDRP, AVDR pacing could be delivered to all of the implanted sites for each paced cycle (either simultaneously or with specified offsets) during the AVDRP, or AVDR pacing could be rotated from one ventricular site to the next during the AVDRP. For example, if there are four ventricular pacing sites, AVDR pacing could be delivered to a first site for the first 25% of the AVDRP, to a second site for the next 25% of the AVDRP, etc., where the percentage of time each site is paced may or may not be evenly distributed. Periodic switching to the AVDR mode may be started immediately following an incident event (e.g. an MI or heart failure decompensation), or the device may be programmed automatically wait a certain period of time (e.g. 30 days post-MI) to initiate the mode switching.

7. Other Embodiments

As described above, AVDR pacing may be used to simulate exercise by intentionally causing asynchronous ventricular contractions. As described in co-pending U.S. patent application Ser. No. 11/559,131, filed on Nov. 13, 2006, asynchronous contractions may also be produced in other ways such as by pacing different sites at different times to cause the heart to contract in an inefficient way, and the embodiments described herein may be combined with any of the embodiments described in that application. Also, some patients may exhibit intrinsic asynchrony and therefore be treated with some kind of pacing therapy that results in more coordinated contractions (e.g., cardiac resynchronization therapy), and simulated exercise may be produced by simply turning off such pacing for some period of time. For such patients, any of the embodiments described herein may be modified by replacing the AVDR mode with a mode in which pacing is ceased and intrinsic contractions are allowed to occur.

U.S. patent application Ser. Nos. 11/561,049, filed on Nov. 17, 2006, now issued as U.S. Pat. No. 7,941,216, describes methods and apparatus for treating myocardial ischemia in which the stress experienced by a myocardial region identified as vulnerable to becoming ischemic is either mechanically loaded or unloaded with pre-excitation pacing. The embodiments described herein for pacing in an AVDR mode may be combined with any of the embodiments described in the 11/561,049, now issued as U.S. Pat. No. 7,941,216, for loading or unloading a vulnerable myocardial region.

The invention has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. A cardiac device, comprising:
sensing circuitry for receiving electrogram signals representing atrial and ventricular activity;
pacing circuitry for delivering atrial and ventricular pacing pulses;
a controller programmed to operate the device in either a normal operating mode or AV delay reduction (AVDR) mode, wherein the normal mode and the AVDR modes are atrial-triggered or AV sequential pacing modes in which paces are delivered to one or more ventricular sites after an AV delay interval with respect to an atrial sense or pace;
wherein, in the AVDR mode, the controller is programmed to deliver paces to the one or more ventricular sites using an AV delay interval that is shorter than the AV delay interval used in the normal mode;
wherein the controller is programmed to intermittently switch from the normal operating mode to the AVDR mode according to a one or more specified entry conditions and switch from the AVDR mode to the normal operating mode according to one or more specified exit conditions;
an impedance sensor for detecting pulmonary edema;
wherein the controller is programmed to operate in the AVDR mode only if pulmonary edema is not detected and use a determination that pulmonary edema has been detected as an exit condition for exiting the AVDR mode.

2. The device of claim 1 wherein the controller is programmed to measure a patient's intrinsic atrio-ventricular interval and compute the AV delay interval used in the AVDR mode as a specified percentage thereof in order to reduce atrial preloading of the ventricles during diastole.

3. The device of claim 1 wherein one or more of the specified entry or exit conditions is a lapsed time interval to cause periodic switching to the AVDR mode.

4. The device of claim 1 further comprising a sensor for measuring a patient's exertion level and wherein the controller is programmed to operate in the AVDR mode only if the measured exertion level is within a specified range.

5. The device of claim 1 wherein the controller is programmed to eliminate the AV delay interval in the AVDR mode.

6. The device of claim 1 further comprising a sensor for measuring pulmonary arterial pressure and wherein the controller is programmed to operate in the AVDR mode only if pulmonary arterial pressure is within a specified range.

7. The device of claim 1 wherein one or more of the specified entry or exit conditions is a command to enter or exit the AVDR mode received via telemetry or a patient-operated switch.

8. The device of claim 1 wherein the controller is programmed to use different pacing channels in the AVDR mode than in the normal operating mode.

9. The device of claim 1 wherein the controller is programmed to deliver pacing through multiple ventricular pacing channels for each paced cycle, either simultaneously or with one or more specified offsets, during the AVDR mode.

10. The device of claim 1 wherein the controller is programmed to deliver pacing through multiple ventricular pacing channels during the AVDR mode, where the multiple ventricular pacing channels are rotated according to a defined schedule.

11. A method, comprising:

delivering pacing pulses to one or more ventricular sites in either a normal operating mode or AV delay reduction (AVDR) mode;

wherein the normal mode and the AVDR modes are atrial-triggered or AV sequential pacing modes in which paces are delivered to one or more ventricular sites after an AV delay interval with respect to an atrial sense or pace;

wherein, in the AVDR mode, paces are delivered to the one or more ventricular sites using an AV delay interval that is shorter than the AV delay interval used in the normal mode and also shorter than a patient's measured intrinsic AV interval;

intermittently switching from the normal operating mode to the AVDR mode according to a one or more specified entry conditions and switching from the AVDR mode to the normal operating mode according to one or more specified exit conditions; and, operating in the AVDR mode only if pulmonary edema is not detected and using a determination that pulmonary edema has been detected as an exit condition for exiting the AVDR mode.

12. The method of claim 11 further comprising measuring a patient's intrinsic atrio-ventricular interval and computing the AV delay interval used in the AVDR mode as a specified percentage thereof in order to reduce atrial preloading of the ventricles during diastole.

13. The method of claim 11 wherein one or more of the specified entry or exit conditions is a lapsed time interval to cause periodic switching to the AVDR mode.

14. The method of claim 11 further comprising measuring a patient's exertion level and operating in the AVDR mode only if the measured exertion level is within a specified range.

15. The method of claim 11 further comprising using different pacing channels in the AVDR mode than in the normal operating mode.

16. The method of claim 11 further comprising delivering pacing through multiple ventricular pacing channels for each paced cycle, either simultaneously or with one or more specified offsets, during the AVDR mode.

17. The method of claim 11 further comprising delivering pacing through multiple ventricular pacing channels during the AVDR mode, where the multiple ventricular pacing channels are rotated according to a defined schedule.

18. The method of claim 11 further comprising eliminating the AV delay interval in the AVDR mode.

19. The method of claim 11 further comprising measuring pulmonary arterial pressure and operating in the AVDR mode only if pulmonary arterial pressure is within a specified range.

20. The method of claim 11 wherein one or more of the specified entry or exit conditions is a command to enter or exit the AVDR mode received via telemetry or a patient-operated switch.

* * * * *